(12) United States Patent
Elmén et al.

(10) Patent No.: US 11,123,489 B2
(45) Date of Patent: Sep. 21, 2021

(54) MEDICAMENT DELIVERY DEVICE (71) Applicant: SHL MEDICAL AG, Zug (CH)

(72) Inventors: Gunnar Elmén, Huddinge (SE); Sebastian Karlsson, Stigtomta (SE)

(73) Assignee: SHL MEDICAL AG, Zug (CH)

( * ) Notice: Subject to any disclaimer, the term of this patent is extended or adjusted under 35 U.S.C. 154(b) by 238 days.

(21) Appl. No.: 16/312,176

(22) PCT Filed: Jun. 22, 2017

(86) PCT No.: PCT/EP2017/065397
§ 371 (c)(1),
(2) Date: Dec. 20, 2018

(87) PCT Pub. No.: WO2017/220725
PCT Pub. Date: Dec. 28, 2017

(65) Prior Publication Data
US 2019/0275255 A1 Sep. 12, 2019

(30) Foreign Application Priority Data

Jun. 23, 2016 (SE) .................... 1650907-7

(51) Int. Cl.
A61M 5/20 (2006.01)
A61M 5/24 (2006.01)
A61M 5/315 (2006.01)
A61M 5/19 (2006.01)

(52) U.S. Cl.
CPC ............ A61M 5/2066 (2013.01); A61M 5/19 (2013.01); A61M 5/24 (2013.01); A61M 5/2448 (2013.01); A61M 5/31515 (2013.01)

(58) Field of Classification Search
CPC ........ A61M 5/19; A61M 5/24; A61M 5/2448; A61M 5/2066; A61M 5/31515; A61M 5/31513; A61M 5/31511
See application file for complete search history.

(56) References Cited

U.S. PATENT DOCUMENTS 4,755,169 A 7/1988 Sarnoff et al.
6,319,225 B1 11/2001 Sugita et al.
(Continued)

FOREIGN PATENT DOCUMENTS

CN 102076371 A 5/2011
CN 104349808 A 2/2015
(Continued)

OTHER PUBLICATIONS

International Search Report and Written Opinion for Int. App. No. PCT/EP2017/065397, dated Oct. 17, 2017.
(Continued)

Primary Examiner — Nathan R Price
Assistant Examiner — Justin L Zamory
(74) Attorney, Agent, or Firm — McDonnell Boehnen Hulbert & Berghoff LLP (57) ABSTRACT A medicament delivery device is presented having a second housing part, a plunger rod arranged in the second housing part and configured to act on a stopper arranged inside a multi-chamber container. A first housing part contains the multi-chamber container, where the first housing part is arranged to be manually displaced into the second housing part by relative rotation between the first and the second housing parts for mixing at least two substances arranged inside the multi-chamber container. The delivery device further has a rotating contact element arranged between said plunger rod and said stopper capable of rotating in relation to said plunger rod.

5 Claims, 6 Drawing Sheets

(56) References Cited

U.S. PATENT DOCUMENTS

| | | |
|---|---|---|
| 6,793,646 B1 | 9/2004 | Giambattista et al. |
| 6,893,420 B2 | 5/2005 | Arnisolle |
| 2009/0259181 A1 | 10/2009 | Moser |
| 2011/0087163 A1* | 4/2011 | Elmen ............... A61M 5/2066 604/82 |
| 2015/0080811 A1 | 3/2015 | Wieselblad |
| 2015/0198248 A1* | 7/2015 | Kiilerich ........... A61M 5/31515 92/172 |
| 2016/0008548 A1 | 1/2016 | Plumptre et al. |
| 2016/0015901 A1 | 1/2016 | Plumptre |
| 2016/0015904 A1 | 1/2016 | Plumptre et al. |

FOREIGN PATENT DOCUMENTS

| | | |
|---|---|---|
| CN | 104780958 A | 7/2015 |
| CN | 105050640 A | 11/2015 |
| EP | 2493532 A2 | 9/2012 |
| JP | 2014-525299 A | 9/2014 |
| KR | 20150008109 A | 1/2015 |
| TW | 201402168 A | 1/2014 |
| WO | 2004/004809 A1 | 1/2004 |
| WO | 2007/115424 A1 | 10/2007 |
| WO | 2009/147026 A1 | 12/2009 |
| WO | 2010/123439 A1 | 10/2010 |
| WO | 2011/051366 A2 | 5/2011 |
| WO | 2012/030276 A1 | 3/2012 |

OTHER PUBLICATIONS

Chinese Office Action for CN Application No. 201780036425.X, dated Mar. 17, 2021.

European Examination Report for EP Application No. 17732419.1, dated Jun. 25, 2021.

* cited by examiner

Fig. 5 ns of these applications are herewith incorporated by
MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2017/065397 filed Jun. 22, 2017, which claims priority to Swedish Patent Application No. 1650907-7 filed Jun. 23, 2016. The entire disclosure contereference into the present application.

TECHNICAL FIELD

The present disclosure relates to an injector for administering, dispensing or delivering medicaments in a safe and reliable way. More particularly, it relates to injection device for manually penetrating a needle arranged to said device and automatic injecting a drug mixture from a multiple chamber container.

BACKGROUND

There are a type of medicaments that can be stored for a long time and that are filled in containers as e.g. cartridges, syringes, ampoules, canisters or the like, containing a ready-to-use medicament in liquid state. However, there are also other type of medicaments that are a mixture of two substances, a medicament agent (e.g. lyophilized, powdered or concentrated liquid) and a diluent (e.g. water, dextrox solution or saline solution), wherein these type of medicaments cannot be pre-mixed and stored for a long time because the medicament agent is unstable and can be degraded and loses its effect quickly. Hence, a user, e.g. a patient himself/herself, a physician, a nurse, hospital personnel or trained persons, has/have to perform the mixing within a limited time period prior to the delivery of a dose of medicament to a patient. Further, some medicament agents are subject to meet significant chemical changes while mixing. Such sensitive medicament agents require a particular treatment so that, when mixing said medicament agents with a diluent, unreasonable mixing force will degrade said medicament agents.

In order to facilitate the mixing, a number of containers for mixing have been developed comprising at least two chambers, known as multi-chamber containers. These multi-chambered containers comprise a first chamber containing the medicament agent and at least a second chamber containing the diluent. These chambers are sealed off with stoppers in order that the medicament agents do not become degraded. When the medicament agent is to be mixed shortly before administering, redirecting passages are opened between the chambers, usually by depressing a distal stopper and in turn a divider stopper of the container somewhat. The passages allow the mixing of the medicament agent and the diluent and the medicament is ready for delivery.

The above mentioned requirements can be achieved by simple medicament delivery devices, such as a common hypodermic syringe, but the procedure is of course rather awkward, in particular for users not used to handle these devices. In order to facilitate for the patient themselves to administer the medicament with a predetermined dose in an easy, safe and reliable way and also to facilitate the administration of medicaments for hospital personnel in the same facilitated way, a number of automatic and semi-automatic devices have been developed in combination with these multiple-chamber solutions for obtaining a mixing before delivery.

A self-injection device arranged with a dual-chamber container, wherein both the mixing and the injection are done automatically by mechanical means, as springs and other means, is disclosed in U.S. Pat. No. 4,755,169. A similar solution is disclosed in U.S. Pat. No. 6,793,646 wherein the mixing of a dual-chamber cartridge is done is done automatically by springs upon activation of the device and the injection is done by manually applying a force to a plunger rod forwardly. A drawback with these devices is that the mixing force, to which medicament agents are subject to, is too high at the beginning due to Hookes law. Hence, the medicament agents can be degraded.

Another solution is disclosed in WO 2004004809, wherein both the mixing and the injection are done automatically by electronics controlled means. A drawback with this device is that the electronics are dependent on batteries and is very sensitive to noise, moisture, water, etc.; which can result in malfunctions. Even more the manufacture of these devices is more expensive than the manufacture of mechanical devices.

In U.S. Pat. No. 6,319,225 the mixing of a dual-chamber ampoule is done manually. The device is set to be vertical on a flat plane and then a downward press on its proximal case causes a relative upward movement of its plunger rod pressing a stopper of the ampoule with eye observation on actions inside the ampoule, such that a mixing is obtained. Though in U.S. Pat. No. 6,319,225 is disclosed that the best suitable process for mixing a medicament agent with a diluent, is by performing manual control of the diluent flow with adequate slowness which will be monitored by eye observation; a drawback with this device is that the mixing force, to which medicament agents are subject to, can be high if the user is stressed and wants to use the device as soon as possible. Hence, the medicament agents can be degraded.

Moreover, the handling and safety aspects of injector devices, having a certain degree of automatic functions, as well as immediate accessibility in emergency situations are issues that attract a lot of attention when developing this type of devices.

One important safety aspect when handling an auto-injector which is used to achieve a manual mixing and an automatic injection, is the locking of the injection means, e.g. a compressed spring actuating on a plunger rod, before the manual mixing have been completely.

One such a device is disclosed in U.S. Pat. No. 6,893,420 wherein a self-injection device is arranged with a dual-chamber body. The mixing is done manually by a screw-tightening operation and the device comprises locking means for locking a latch means that prevent the automatic penetration and injection means from being released before the mixing has been completely finished. However, this solution is rather bulky and relies also on many components acting in co-operation and in sequence, one triggering another, which may lead to a mal-function, mal-dose accuracy, or that the device becomes complicated, hence not user friendly. This device suffers from the drawback that locking means has to be actively removed from the device after the mixing has been finished. This is a step which is not intuitive for a user, who will try to push the locking means instead of removing them. Another drawback is the dose accuracy, since the penetration starts pushing the stoppers, the medicament will start to be expelled during the whole penetration sequence, leading to so called wet injections and delivering of medicament through the whole penetration tissue instead of injecting the required dose at the intended penetration depth.

Another such a device is disclosed in WO2007/115424A1 which relates to an injection device having a container holder having a multi-chamber container within, which is manually movable relative to the injection device for the purpose of mixing the components within the multi-chamber container. The device further comprises a spring which can bear on a part of the injection device, and a coupling element for coupling the container holder to the spring such that, during the movement of the container holder into the injection device, the spring is tensioned. The device also comprises an activation knob and a push button, wherein the activation knob has to be rotated for forcing the push button to protrude from the housing and thereby setting the device in a ready for injection delivery state. However, this solution suffers from the drawback that the activation knob has to be actively manipulated for releasing the push button after the mixing has been finished. This is a step which is not intuitive for a user, who will try to find where the push button or activation means are located instead of rotating the knob.

Even though the devices according to U.S. Pat. No. 6,893,420 and WO2007/115424A have proved to function well and displays a degree of safety, there is always a desire for improvements of such devices, among them being the design of the mechanism in order to simplify the manufacture and assembly in order to reduce costs but at the same time maintain or even improve the reliability of the safety and function of the device.

Another problem or issue with medicament delivery devices provided with mixing functions that are manually operated is that the proximal end of the plunger rod is in contact with the most distal stopper during the mixing stage. Document WO 2009/147026 discloses a medicament delivery device having two housing parts that are threadedly attached to each other, where a proximal housing part is provided with a medicament container and the distal part is arranged with a dose setting mechanism and a plunger rod. When a mixing is to be performed, the two housing parts are rotated in relation to each other wherein they are moved towards each other. The plunger rod is then acting on the most distal stopper such that a mixing action is obtained in the medicament container. Since the medicament container is in one housing part and the plunger rod is in the other housing part, the most distal stopper and the plunger rod will rotate in relation to each other. This is a disadvantage since there will be frictional forces between them, making it more difficult to perform the mixing but also may affect the material of the most distal stopper in a negative way.

SUMMARY

The aim of this disclosure is to provide an injection device which is uncomplicated and easy to use especially during mixing, and which reduces or minimizes the forces between the plunger rod and the most distal stopper during the mixing action.

This aim is obtained with a medicament delivery device having the features of the independent patent claim. Preferable embodiments of the disclosure form the subject of the dependent patent claims.

According to a main aspect, a medicament delivery device is displayed comprising a second housing part provided with a plunger rod which is configured to act on a stopper arranged inside a multi-chamber container. Further, a first housing part is provided, into which said multi-chamber container is arranged.

The first housing part is arranged to be manually displaced into the second housing part by relative rotation between the first and the second housing parts for mixing at least two substances arranged inside the container. Further, the medicament delivery device comprises a rotating contact element arranged between said plunger rod and said stopper capable of rotating in relation to said plunger rod.

With such a solution, the friction forces between the plunger rod and the most distal stopper are greatly reduced or minimized, leading to a better mixing performance, reduced force needed to rotate the two housing parts and reduced risk of damaging the most distal stopper.

According to one feasible solution, the rotating contact element may comprise a disk provided with a central passage, and wherein said plunger rod is arranged with a shaft arranged to extend through said central passage. The disk is thus journaled on the shaft and may rotate easily whereby the rotational force between the stopper and the plunger rod is greatly reduced.

The medicament delivery device may further comprise drive force means capable of pushing said plunger rod for acting on said stopper. With this solution, the medicament delivery device is provided with an automatic function, facilitating the use of the medicament delivery device.

In order to obtain the desired action between the housing parts during mixing, the inner surface of the second housing part may be arranged with threads corresponding to threads arranged on the outer surface of the first housing part.

Further, the inner surface of the second housing part may be arranged with a number of annular protrusions which are intended to fit into corresponding annular recesses on the outer surface of the first housing part for locking said two housing parts after the substances has been mixed.

These and other aspects of and advantages with the present disclosure will become apparent from the following detailed description and from the accompanying drawings.

BRIEF DESCRIPTION OF THE FIGURES

In the following detailed description of the disclosure, reference will be made to the accompanying drawings, of which

DETAILED DESCRIPTION

In the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

The embodiment shown in the drawings comprises a proximal part 10 and a distal part 20, FIGS. 1-5.

Figure 1:
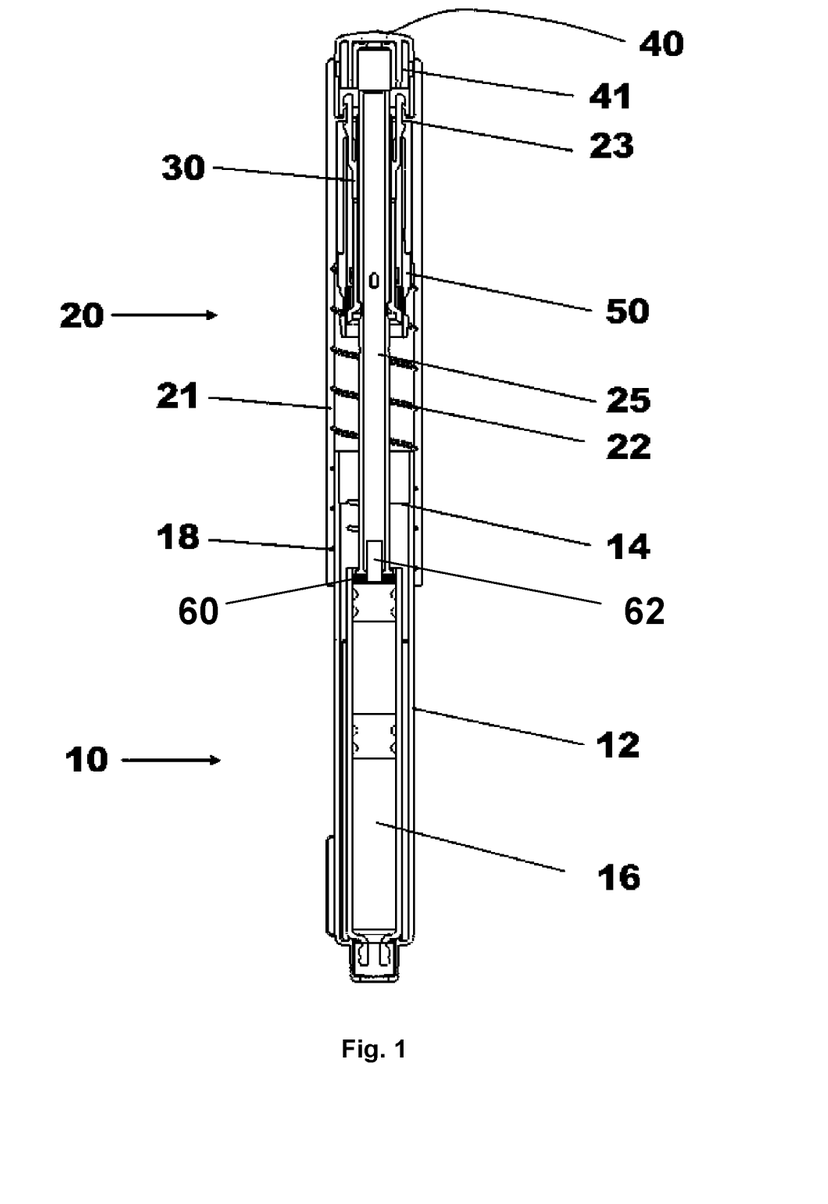
FIG. 1 is a cross-sectional side view of the auto-injector according to the disclosure in a pre-mixed position.

The proximal part 10 comprises a generally tubular first housing part 12 having elongated openings for viewing a multi-chamber container 16 which is arranged inside, FIG. 1, and a somewhat narrowing proximal end. The multi-chamber container 16 comprises at least two medicament substances arranged in each chamber, a distal stopper 17, a proximal stopper 19, and redirecting passages between the chambers. The distal end of the first housing part is arranged with annular threads 18 on its outer surface. Moreover, the distal end is arranged with a neck portion having an inner diameter that is larger than the inner diameter of the rest of the body and thereby creating an annular ledge 14 between these two inner surfaces.

Figure 6:
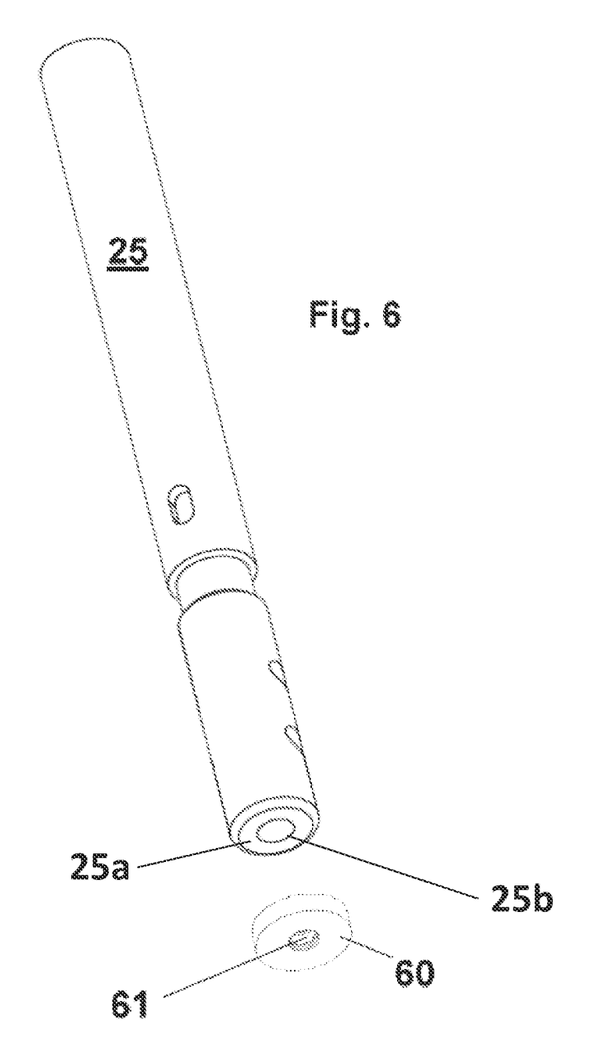
FIG. 6 is a perspective view of a plunger rod and a rotating contact element.

FIGS. 1-5 show the distal part or power unit 20 of the injector according to this disclosure. It comprises a second housing part 21, a plunger rod 25 formed as a tubular member and with an outer diameter somewhat smaller than the inner diameter of the container body to be used, a drive force means, an activation member 30 and a locking member 50. The plunger rod 25 has a terminal proximal end face 25a having an opening 25b, where the plunger rod 25 is arranged with a circumferential groove 26 with a certain width. Inside the plunger rod a drive force means (not shown) e.g. a helical compression spring, is pre-tensioned arranged and inside the spring a spring guide (not shown) is placed, as described below. On the proximal end of the plunger rod, a rotating contact element 60 is arranged such that it may rotate in relation to the plunger rod 25. In the embodiment shown the rotating contact element has a disk-shape with a central passage 61, FIG. 6, through which a shaft 62, FIG. 1, may extend. The shaft 62 is then attached to the terminal proximal end face 25a and opening 25b of the plunger rod 25.

Surrounding the plunger rod is the activation member 30 as e.g. an activator sleeve with a mainly tubular shape. Its proximal end comprises flexible locking means so as to form flexible tongues 39. Each tongue has an inclined transition surface 32 which meets with a band-shaped part 34 with enlarged diameter. On the inner surface adjacent the transition surface an annular inwardly directed ledge 36 is arranged, with a shape as to fit into the groove 26 of the plunger rod for holding the plunger rod and thereby said drive force means in a pre-tensioned state. The activator sleeve is further provided with hook means so as to form at least one flexible tongue 31. Each tongue 31 is arranged with an outwardly directed hook 37 at the outer end and a protrusion 33, with an inclined surface, a distance along each tongue. The distal end of the activator sleeve is arranged with a push button 35 protruding from said second housing part. A cover 40 having two tongues 41 attached to its outer edge and directed in the proximal direction of the device is attached to the push button.

Around the activator sleeve 30, a locking member 50, hereafter named actuator sleeve, also of a generally tubular form, is slidably arranged in relation to said activator between a first position wherein said locking member completely surrounds said locking means and a second position wherein said locking member partially surrounds said locking means after said locking member has been axially displaced by said first housing when said first housing has been displaced into said second housing part, as will be described. The actuator sleeve comprises a distal end with at least one distally extending tongue and a proximal end with a first annular part 52 on its outer surface. At a distance from the first annular part 52, a second annular part 56 ending in a ledge 58 is arranged on the outer surface.

The second housing part 21 is of a generally tubular shape, where the inner surface of the proximal end is arranged with threads 22 corresponding to the threads 18 of the first housing part 12 and provided with a number of annular protrusions which are intended to fit into the corresponding annular recesses on the inner surface of the second housing part 21. Moreover, the inner surface of the second housing part comprises radially holding means. Said radially holding means being an annular ring 23 provided with a circumferential ledge 24 with a shape corresponding to the hook 37 of the activator sleeve.

Further, a compression spring (not shown) is arranged surrounding the actuator sleeve 50 between the annular ring 23 and the second annular part 56 of the actuator sleeve.

The function of the injector according to this disclosure will now be described in connection with the FIGS. 1-4.

The injector will be delivered to the user as shown in FIG. 1, where a multi-chamber container is placed in the first housing part and the second housing part is attached to the proximal part.

Figure 2:
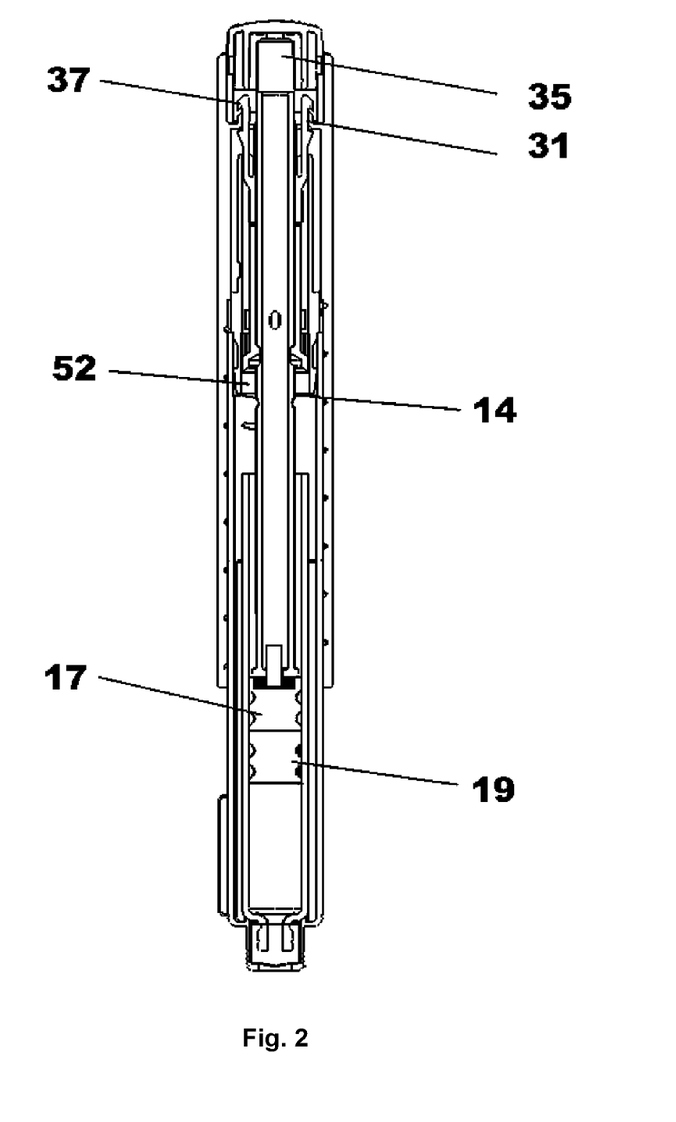
FIG. 2 is a cross-sectional side view of the auto-injector according to the disclosure in a medicament mixed position.
Figure 3:
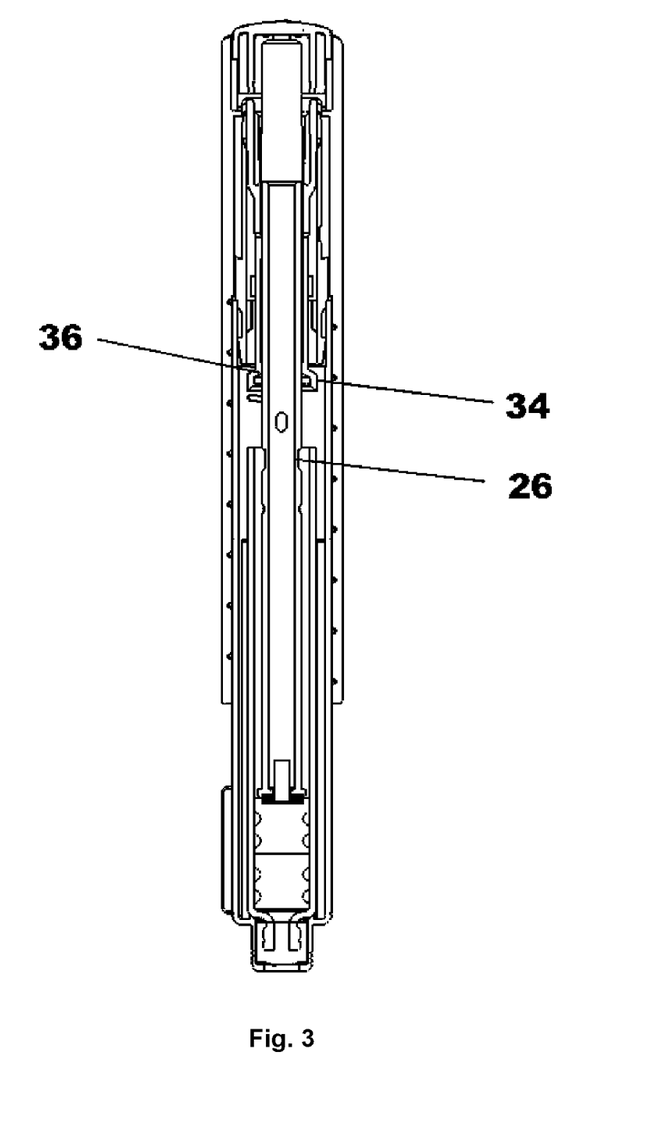
FIG. 3 is a cross-sectional side view of the auto-injector according to the disclosure in a final position.
Figure 4:
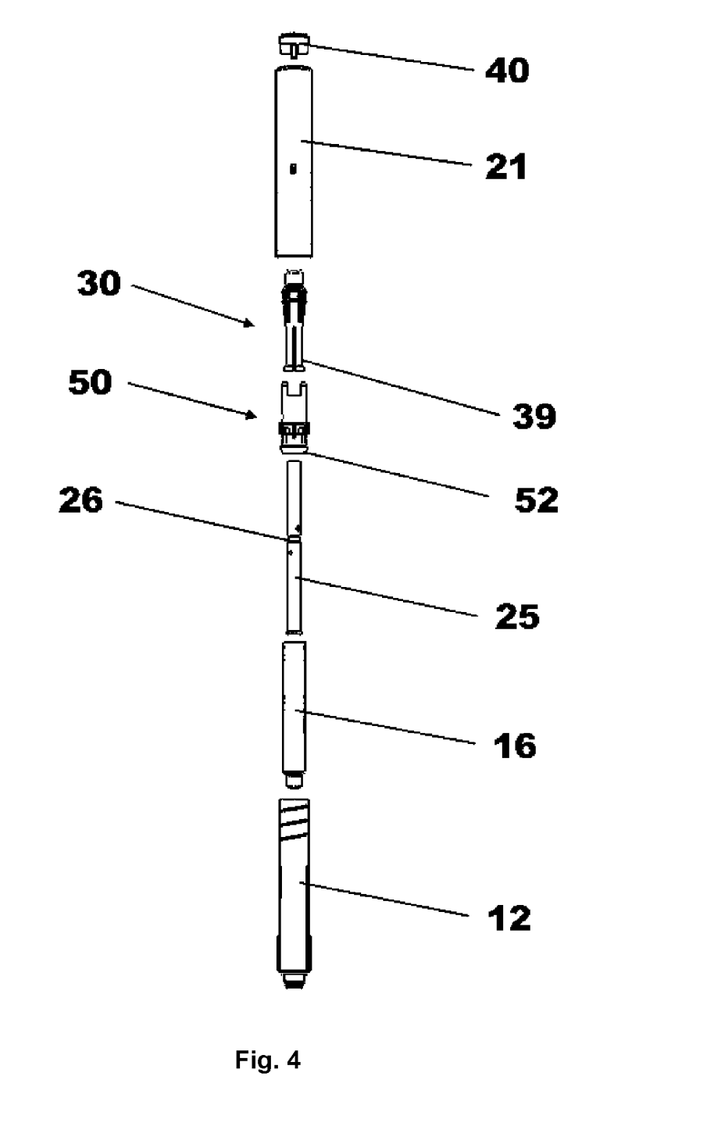
FIG. 4 is an exploded view of the auto-injector according to the disclosure.
Figure 5:
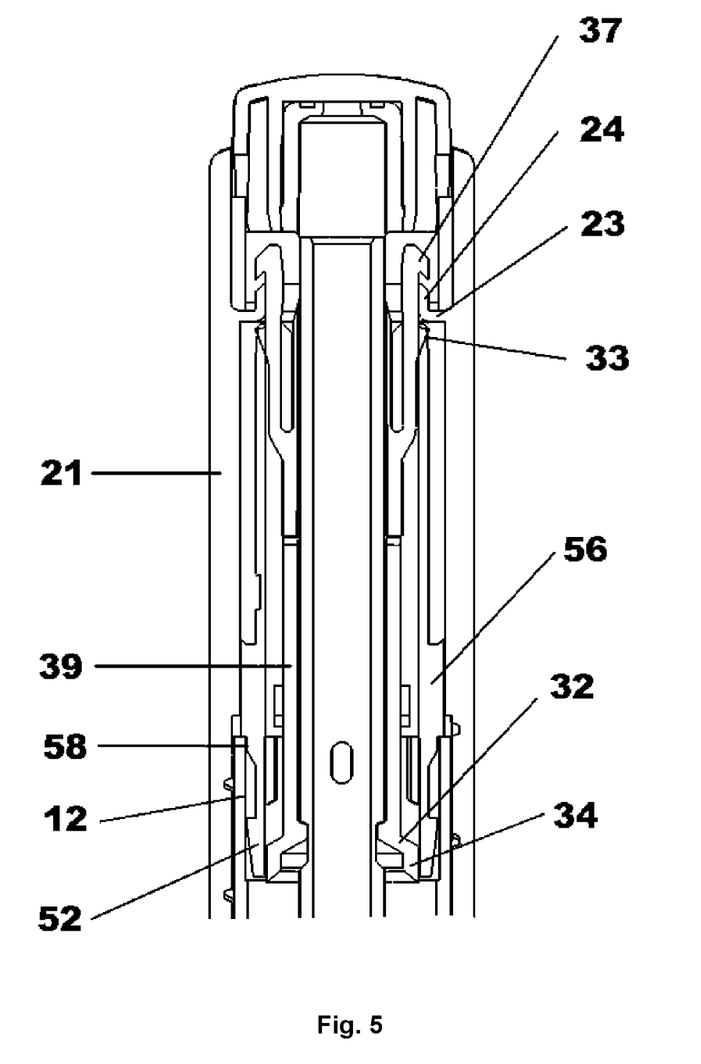
FIG. 5 is a zoomed view of the distal part of the auto-injector according to the disclosure.

When a mixing is to be performed, the first housing part is screwed into the second housing part until the plunger rod, which is static in relation to the container, has shifted the distal stopper axially with respect to the container such that medicament substances inside said multi-chamber container have been completely mixed, see FIG. 2. During the mixing, the rotating contact element 60 is abutting the distal end of the distal stopper and rotating relative to the plunger rod, whereby the rotational friction between the distal stopper and the plunger rod is greatly reduced. In the mixed position, the annular protrusions provided on the first housing part 12 fits into the corresponding annular recesses on the inner surface of the second housing part 21, and thereby locking said two bodies.

At the same time the distal end part of the first housing part 12 surrounds the proximal part of the actuator sleeve 50 such that the distal end ledge 14 of the first housing part 12 comes into contact with the proximal end of the first annular part 52 and with the ledge 58 respectively.

Moreover, when the mixing is performed, the actuator sleeve 50 is pushed axially towards the distal end of the device against the force of the compression spring acting between the second annular part 56 of the actuator sleeve and the annular ring 23 of the second housing part 21. The part of the band-shaped part 34 is then partially situated outside the proximal part of the actuator sleeve. The at least one distally extending tongue of the actuator sleeve will then come in contact with the inclined surface of the protrusion 33 of the at least one tongue 31 on the activator sleeve whereby the hook 37 is moved inwards and are free to pass inside the circumferential ledge 24.

The next step is to connect a needle or a safety pen needle to the proximal end of the first housing part 12 if the container is not a syringe, and to achieve a manual penetration of the needle into an injection site as e.g. the tissue of a patient. When activating the injection, the user merely depresses the cover 40 over the push button, FIG. 3, wherein the tongues 41 axially slides over the at least one flexible tongue 31. This causes the activator sleeve to be moved towards the proximal end of the device whereby the hooks 37 pass inside the circumferential ledge 24 and the band shaped part 34 is completely out of the actuator sleeve. The resilient properties of the tongues 39 of the activator sleeve causes the ledges 36 to move out of the groove 26 of the plunger rod, which then is free to move due to the helical compression spring inside the plunger rod. The force of the compression spring urges the plunger rod to push on the stopper of the container and the liquid medicament is injected into the patient until the stopper reaches the inner proximal end of the container.

It is to be understood that the flexible locking means are arranged to be released from said plunger rod only after said locking member is moved from the first position to the second position and said push button is axially moved into the second housing part, such that the flexible locking means comes completely out of contact with the locking member. If the mixing is not completely performed i.e. the first housing part has not been completely displaced into the second housing part such that said first housing part has not come into contact with said actuator sleeve, then said actuator sleeve has not been axially displaced towards the distal end of the device due to the force exerted by the compression spring arranged between the annular ring 23 and the second annular part 56 of the actuator sleeve. Moreover, if the user attempts to depress the push button before the mixing is completely done, the outwardly directed hooks 37 of the flexible tongues 31 will engage the annular ring 23 for avoiding premature activation of the device.

It is to be understood that the embodiment described above and shown in the drawings is to be regarded as a non-limiting example of this disclosure and that it is defined be the patent claims.

The invention claimed is:

1. A medicament delivery device comprising:
a second housing part;
a plunger rod arranged in said second housing part and configured to act on a stopper arranged inside a multi-chamber container, where the plunger rod comprises a terminal proximal end face;
a first housing part into which said multi-chamber container is arranged, where the first housing part is arranged to be manually displaced into said second housing part by relative rotation between the first and the second housing parts for mixing at least two substances arranged inside said container;
a shaft having a proximal end and a distal end, where the distal end is fixedly attached to the terminal proximal end face of the plunger rod; and
a rotating contact element comprising a disk having a central passage configured so that the disk is journaled to the proximal end of the shaft such that when the rotating contact element engages the stopper during displacement of the first housing part into the second housing part the rotating contact element will rotate with the stopper and relative to the plunger rod and the shaft.

2. The medicament delivery device according to claim 1, further comprising drive force means capable of pushing said plunger rod for acting on said stopper.

3. The medicament delivery device according to claim 1, further characterized in that an inner surface of the second housing part is arranged with threads corresponding to threads arranged on the outer surface of the first housing part.

4. The medicament delivery device according to claim 1, wherein an inner surface of the second housing part is arranged with a number of annular protrusions which are intended to fit into corresponding annular recesses on the outer surface of the first housing part for locking said two housing parts after the substances has been mixed.

5. A medicament delivery device comprising:
a second housing part;
a plunger rod arranged in the second housing part and configured to act on a stopper arranged inside a multi-chamber container, where the plunger rod comprises a terminal proximal end face having an opening;
a first housing part into which the multi-chamber container is arranged, where the first housing part is arranged to be manually displaced into the second housing part by relative rotation between the first and the second housing parts for mixing at least two substances arranged inside the container;
a shaft having a proximal end and a distal end, where the distal end is attached within the opening; and
a rotating contact element comprising a disk having a central passage configured so that the disk is journaled to the proximal end of the shaft such that when the rotating contact element engages the stopper during displacement of the first housing part into the second housing part the rotating contact element will rotate with the stopper and relative to the plunger rod and the shaft.

* * * * *